(12) United States Patent
Frech et al.

(10) Patent No.: US 6,552,786 B1
(45) Date of Patent: Apr. 22, 2003

(54) ELECTROTHERMAL FURNACE FOR AN ATOMIC ABSORPTION SPECTROMETER

(75) Inventors: Wolfgang Frech, Umeå (SE); Lars Lundmark, Bygdsiljum (SE); Bernhard Radziuk, Frickingen (DE); Rolf G. M. Tamm, Salem (DE)

(73) Assignee: Berthold GmbH & Co. KG (DE)

( * ) Notice: Subject to any disclaimer, the term of this patent is extended or adjusted under 35 U.S.C. 154(b) by 241 days.

(21) Appl. No.: 09/653,022

(22) Filed: Sep. 1, 2000

(30) Foreign Application Priority Data

Sep. 2, 1999 (DE) .......................................... 199 41 874

(51) Int. Cl.[7] .............................................. G01N 21/74
(52) U.S. Cl. ...................................................... 356/312
(58) Field of Search .......................................... 356/312

(56) References Cited

U.S. PATENT DOCUMENTS

| 4,175,863 A | 11/1979 | Tamm et al. | 356/312 |
|---|---|---|---|
| 4,580,899 A | 4/1986 | Wiseman et al. | 356/312 |
| 5,066,123 A | 11/1991 | Tamm et al. | 356/312 |

FOREIGN PATENT DOCUMENTS

| DE | 2617928 | 10/1977 |
|---|---|---|
| DE | 2710864 | 9/1978 |
| DE | 3228245 | 2/1983 |
| DE | 3534417 | 4/1987 |
| DE | 3907454 | 9/1990 |

OTHER PUBLICATIONS

W. Frech and S. Jonsson, "A New Furnace Design For Constant Temperature Electrothermal Atomic Absorption Spectroscopy", Spectrochimica Acta vol. 37B, No. 12, May 1992, pp. 1021 through 1028.

W. Frech, "Recent Developments In Atomizers For Electrothermal Atomic Absorption Spectrometry", Fresenius J Anal Chem, Feb. 1996, pp. 475 through 486.

*Primary Examiner*—F. L. Evans
(74) *Attorney, Agent, or Firm*—St. Onge Steward Johnston & Reens, LLC

(57) ABSTRACT

The present invention relates to a thermoelectrical furnace for an atomic absorption spectrometer for converting a sample to be analyzed into the atomized state, the furnace comprising a first hollow furnace part connected to a first pair of electrodes and including a first opening for introducing the sample, and a second hollow furnace part connected to a second pair of electrodes and including a second opening for introducing the sample. Said furnace is characterized in that the first furnace part and the second furnace part are each mounted on holders that are movable between a first position and a second position such that in the first position the first furnace part can be fed with the sample and that in the second position the openings of the first and second furnace parts are aligned such that the sample can be transferred from the first furnace part into the second furnace part, wherein a distance required for electrical and thermal decoupling between the first and the second furnace parts is reproducibly defined.

15 Claims, 3 Drawing Sheets

ELECTROTHERMAL FURNACE FOR AN ATOMIC ABSORPTION SPECTROMETER

BACKGROUND OF THE INVENTION

1. Field of the Invention

The present invention relates to an electrothermal furnace for an atomic absorption spectrometer for converting a sample to be analyzed into the atomic state, the furnace comprising a first hollow furnace part connected to a first pair of electrodes and including a first opening for introducing the sample, and a second hollow furnace part connected to a second pair of electrodes and including a second opening for introducing the sample.

2. Description of the Related Art

Such an electrothermal furnace is well known in the prior art. The advantages which are achieved in spectroscopic analyses with a two-part electrothermal furnace of the above-described type are illustrated in detail in the literature. A corresponding two-part furnace, also designated as a "two-step furnace", consists of a graphite tube which is arranged directly above a graphite container receiving the sample. In the tube surface opposite to the container, there is provided an opening which is aligned with the position of the container and corresponds to the diameter thereof, the graphite tube and the container being however spaced apart from each other. The graphite tube and the container can be heated separately, the graphite tube being in general first heated to the desired high operating temperature and then the container with the sample. After vaporization the various components of the sample pass through the opening into the graphite tube by reason of the thermal movement of the atoms. The gap between the graphite tube and the container produces losses due to atoms exiting from the gap, whereby the efficiency of the analysis is impaired. To create reproducible analytical conditions, the positions of the graphite tube and the container are fixed mechanically. The relative position of the two furnace parts to one another is thereby defined. In such an arrangement the sample is passed by means of a suitable automatic device to the container via a dosing opening positioned at the accessible upper side of the graphite tube. Said dosing opening, however, reduces the sensitivity of the spectrometer because of diffusing sample atoms.

Furthermore, the alignment of the automatic device for the introduction of the sample is difficult. Furthermore, with the known exemplary electrothermal furnace, a spectroscopic analysis with an increased or reduced ambient pressure can only be carried out by way of a manual introduction of the sample using a bulky and complex vacuum or pump means.

SUMMARY OF THE INVENTION

It is the object of the present invention to improve the known electrothermal furnace with respect to the above-mentioned drawbacks.

Said object is achieved for an electrothermal furnace of the above-mentioned type by the measures that the first furnace part and the second furnace part are each mounted on holders that are movable between a first position and a second position such that in the first position the first furnace part can be fed with the sample and that in the second position the openings of the first and second furnace parts are aligned relative to each other such that the sample can be transferred from the first furnace part into the second furnace part, wherein a distance required for electrical and thermal decoupling between the first furnace part and the second furnace part is reproducibly defined.

With the inventive construction of the electrothermal furnace, the first furnace part can be fed with a sample such that the holders respectively receiving the first and second furnace parts are located in the second position. Thus, an additional dosing opening with the disadvantages entailed thereby, as is the case in the prior art, is not necessary. Furthermore, the second position of the holding means ensures that the mechanical fixation of the furnace parts is reproducible. Hence, there are reproducible analyzing conditions with respect to the light beam passing through the second furnace part and also with respect to the thermal transportation of the atomized sample components. A further advantage of the inventive electrothermal furnace is that the distance required for electrical and thermal decoupling can be minimized between the first and second furnace parts due to the exact and reproducible fixation of the holder in the second position, whereby the sensitivity of the spectrometer is improved in comparison with the prior art.

Advantageously, the holders are each made rotatable or pivotable or linear relative to one another or are made movable in any desired combination thereof, the holders being only movable along a defined connection path.

This has the advantage that the holders are movable relative to each other by easily producible elements, e.g. pivot joints or rails.

In a further embodiment of the invention, one of the holders is connected to a drive element for automatically transferring the first and second furnace parts into the first position and second position, respectively.

It is thus possible to automate the feeding operation while maintaining the mechanical accuracy, and thus to increase the number of the analyzed samples per unit of time.

Advantageously, the drive element comprises a pneumatic or electric drive unit. Hence, an atomization can be realized in a simple and inexpensive manner with a simple activation means which may be controlled by an operator or by a program.

In a further development, the first furnace part is arranged in a first recess in one of the holders and the second furnace part is arranged in a second recess in the other holder, the first and second recesses in the second position forming a combined cavity which is gas-tightly sealed to the surroundings.

This arrangement has the advantage that the first and second furnace parts can be acted upon with a reduced or elevated pressure, and that the sample can be analyzed under desired pressure conditions without requiring a bulky and complex vacuum or pump device.

Advantageously, the holders comprise a spacer which mechanically defines the second position. The necessary distance between the first and second furnace parts and the alignment of the first and second openings can thereby be designed easily.

In a further embodiment, the spacer comprises an elevated ring defining the first recess and including a seal on one of the holders, and a recess corresponding to the elevated ring with the seal and provided on the other holder.

Advantageously, the mechanical position of the two holders relative to one another and thus the position of the two openings are on the one hand ensured by the seal on the elevated ring in the radial direction, and the distance between the first and second furnace parts is fixed on the other hand while the seal simultaneously seals the first and second furnace parts in a gas-tight manner to the surroundings.

In a further embodiment, the spacer comprises a guide pin on one of the holders, and a guide bushing accurately matching the guide pin and provided on the other holder. The advantage of such an arrangement consists in the simple and inexpensive producibility of the spacer.

Advantageously, either the first or the second recess comprises at least one fluid supply opening. The sample to be analyzed can thus be subjected to an elevated or reduced pressure, and it is also possible to introduce additional gases, such as argon, into the first and/or second furnace part.

In a further advantageous design, the first pair of electrodes is connected in a gas-tight manner to one of the holders, and the second pair of electrodes to the other holder. This arrangement permits the use of discrete replaceable electrodes; a gas-tight seal of the first and second furnace parts to the surroundings is here possible at the same time.

Advantageously, the holders comprise a cooling element.

BRIEF DESCRIPTION OF THE DRAWINGS

The invention shall now be explained in detail with reference to a preferred embodiment shown in the drawings, in which.

DETAILED DESCRIPTION OF THE INVENTION

Figure 1:
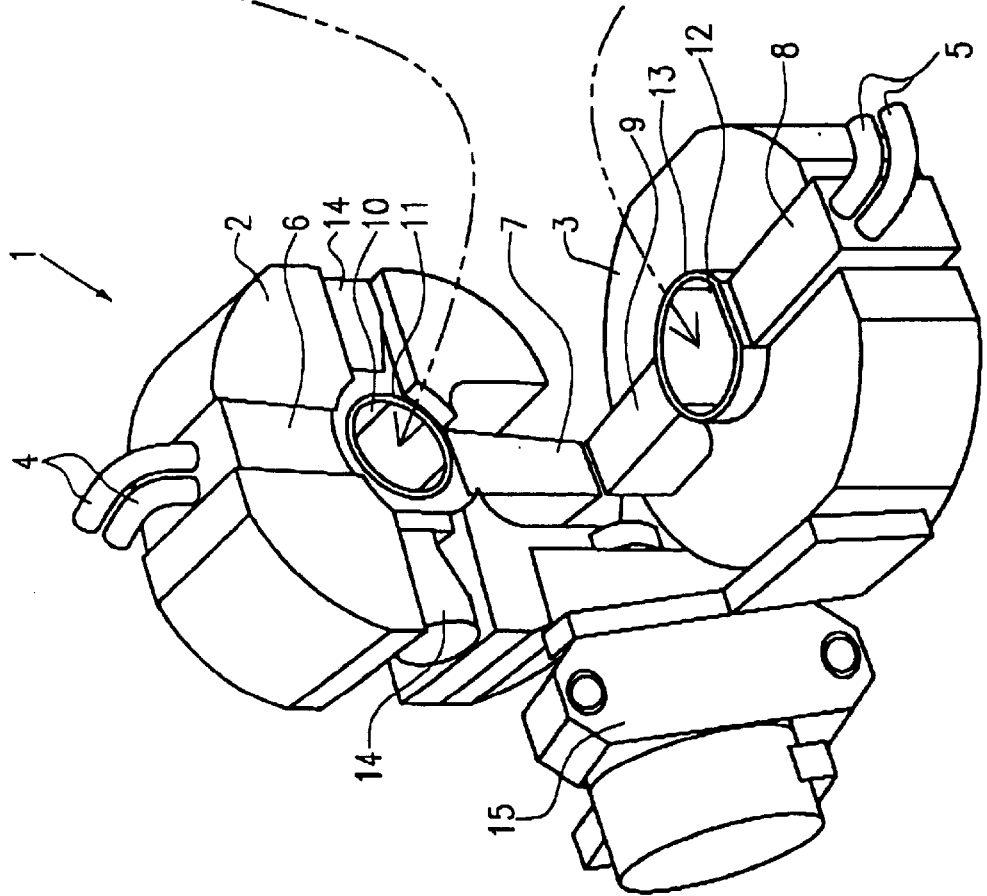
FIG. 1 is a perspective three-dimensional view of a preferred embodiment of the invention.

FIG. 1 is a perspective three-dimensional view showing the preferred embodiment of the invention. Reference numeral 1 designates the electrothermal furnace of the invention in a first position in which the furnace 1 can be loaded with a sample. In FIG. 1, respective holders 2 and 3 are shown at an angle relative to one another in a tilted position. The holder 2 comprises the electrode blocks 6 and 7, and cooling-water connections 4 are provided on electrode 6. By analogy, the holder 3 comprises the electrode blocks 8 and 9, and cooling water connections 5 are provided on electrode 8. In this embodiment, the holders 2 and 3 as well as the electrode blocks 6, 7 and 8, 9 are made in a uniform manner from the same material, e.g. brass. However, it is also possible to use different material components for the holder and the electrodes. Electrically and thermally highly conductive materials are here preferred. In the center of the holder 2, there is a cylindrical recess 10 which is radially defined by a rim 11. By analogy, the holder 3 is provided in the center with a cylindrical cavity 12 which is radially defined by a rim 13 that is provided on its upper edge with a seal. Furthermore, in the holder 2, the electrodes 6 and 7 as well as the rim 11 are offset rearwards in comparison with the forwardly oriented surface of the holder 2 in FIG. 1. By contrast, the electrodes 8 and 9 and the rim 13 are projecting upwards relative to the upwardly oriented surface of the holder 3 in FIG. 1. The holder 2 is divided into two portions by the recess 10 and the tubes 14 which are opposite to each other at 180°. The tubes 14 are connected to the recess 10 and sealed to the outside with respective quartz windows and suitable heat-resistant O-rings.

Together with the recess 10 the tubes 14 form the optical axis for the light beam for analyzing the sample. The holders 2 and 3 are connected to a rotary drive unit 15 whose rotational axis in the present embodiment is in parallel with the optical axis.

Upon activation of the rotary drive unit 15, the holder 2 is transferred from the first position shown in FIG. 1 into a second position in such a manner that the respectively opposite surfaces of the holders 2 and 3 are in parallel and spaced apart, thereby forming the second position of the electrothermal furnace. The exact position of the holders 2 and 3 relative to each other is ensured by the seal which is integrated into rim 13 and consists of an electrically insulating material.

Figure 2A:
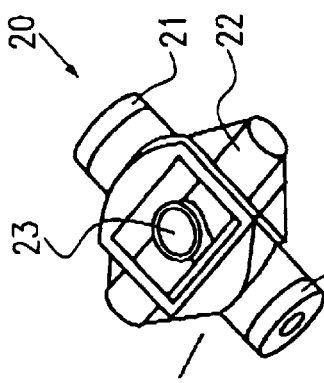
FIGS. 2a and 2b show each a detail of the embodiment illustrated in FIG. 1.

FIG. 2a is a perspective view showing a second furnace part 20 which is mounted in the recess 10 in holder 2. The second furnace part 20, which is made from graphite, has electrode connections 21 for transversely heating a sample detection tube 22 through which the light beam is axially passing during analysis. Furthermore, the second furnace part 20 comprises a second opening 23 which communicates with the sample detection tube 22.

Figure 2B:
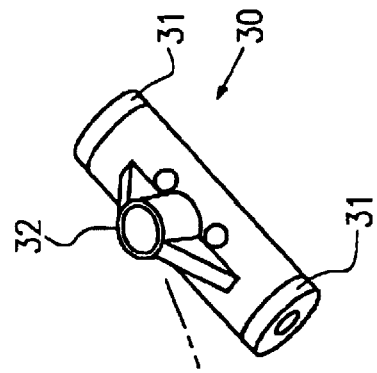

FIG. 2b is a perspective view showing a first furnace part 30 which is mounted in the cylindrical cavity 12 of holder 3. The furnace part which is made from graphite comprises electrode connections 31 at both ends. A cup 32 which forms a cylindrical interior is mounted on the outer wall of the first furnace part 30. The cup 32 is preferably designed such that a uniform temperature distribution is achieved while current is flowing through the cup 32. In the first position shown in FIG. 1, the cup 32 can simply be fed with a solid or liquid sample. In the second position where the holders 2 and 3 are in parallel with each other, the second furnace part 20 and the first furnace part 30 are oriented relative to one another at a small distance such that the opening of the cup 32 is in alignment with the second opening 23.

Figure 3:
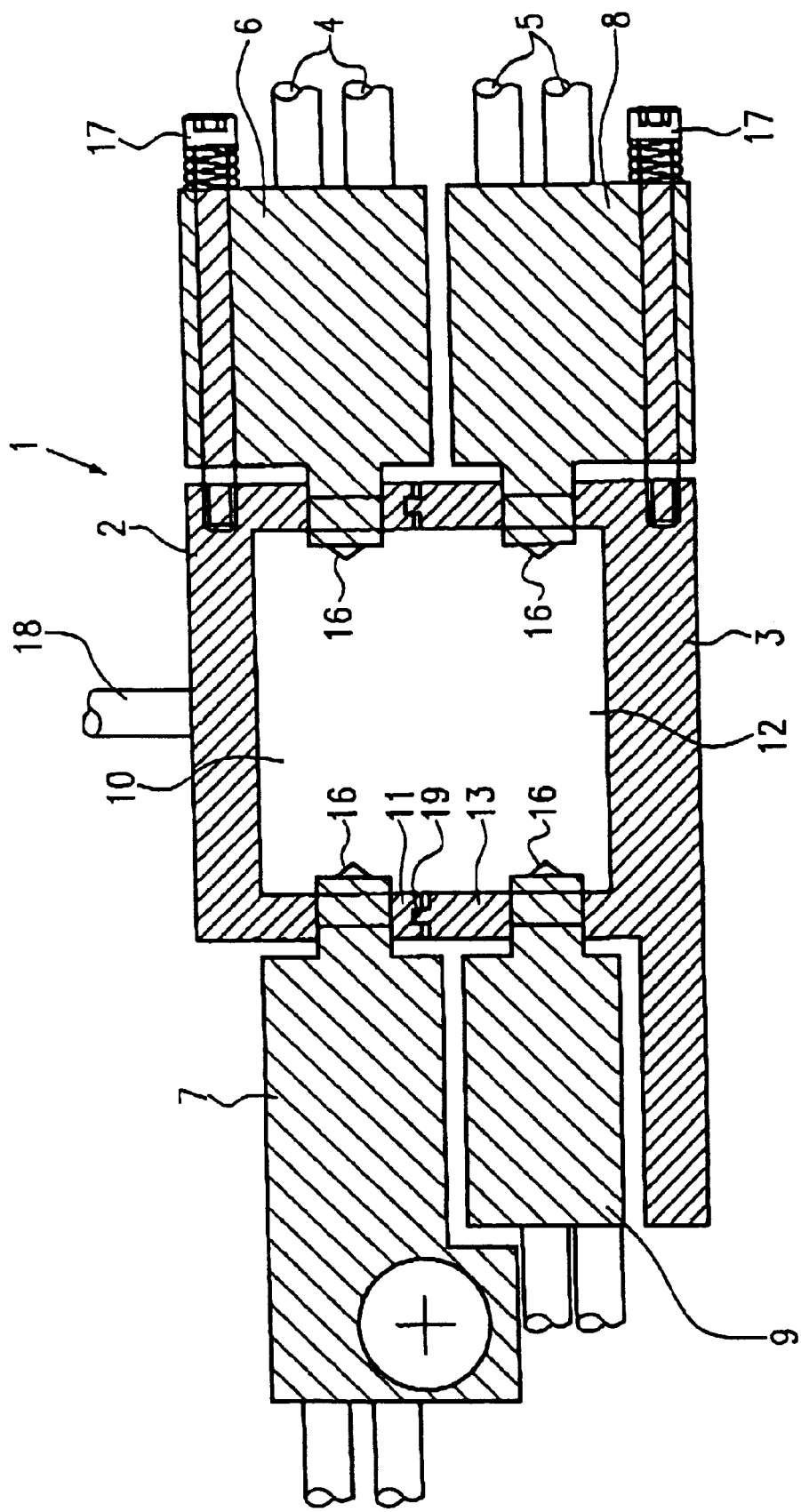
FIG. 3 is a schematic cross-section through the embodiment illustrated in FIG. 1.

FIG. 3 is a schematic view showing a cross section through the embodiment illustrated in FIG. 1 along electrodes 8, 9 and 6, 7 when the furnace 1 is in the second position. The figure shows the assembly without the first and second furnace parts 30, 20. In FIG. 3, members which are identical with those of FIG. 1 are provided with identical reference numerals. In FIG. 3, each of the electrodes 6, 7 and 8, 9 is provided with graphite connections 16 in the radially inwardly oriented direction relative to holders 2 and 3. Furthermore, apart from the cooling-water connections 4 and 5, the electrodes 6 and 8 comprise adjusting screws 17 provided with springs. The adjusting screws 17 mechanically preload the movable electrodes 6 and 7, thereby enabling the electrodes 6 and 7 to recede, on condition that these are acted upon with a pressure exceeding the preload. Furthermore, the recess 10 together with the cylindrical cavity 12, the rim 13 and the border 11 defines a volume which is sealed in gas-tight fashion by a seal 19 relative to the surroundings. The seal 19, which is formed as a heat-resistant O-ring made from electrically insulating material, simultaneously prevents a direct mechanical contact between rim 11 and rim 13. Furthermore, the electrodes 6, 7 and 8, 9 are each sealed in gas-tight fashion with suitable seals (not shown in FIG. 3) relative to the volume formed by the recess 10 and the cylindrical cavity 12. Furthermore, a connection piece 18 makes it possible to apply reduced or elevated pressure to the volume formed by the recess 10 and the cylindrical cavity 12. Optionally, there may be provided further connection pieces which e.g. permit the supply of a gas. Alternatively, gas may also be supplied through the electrodes. The rotational axis of the rotary drive 15, which is not shown in FIG. 3, is marked by the marking in electrode 7.

Figure 4:
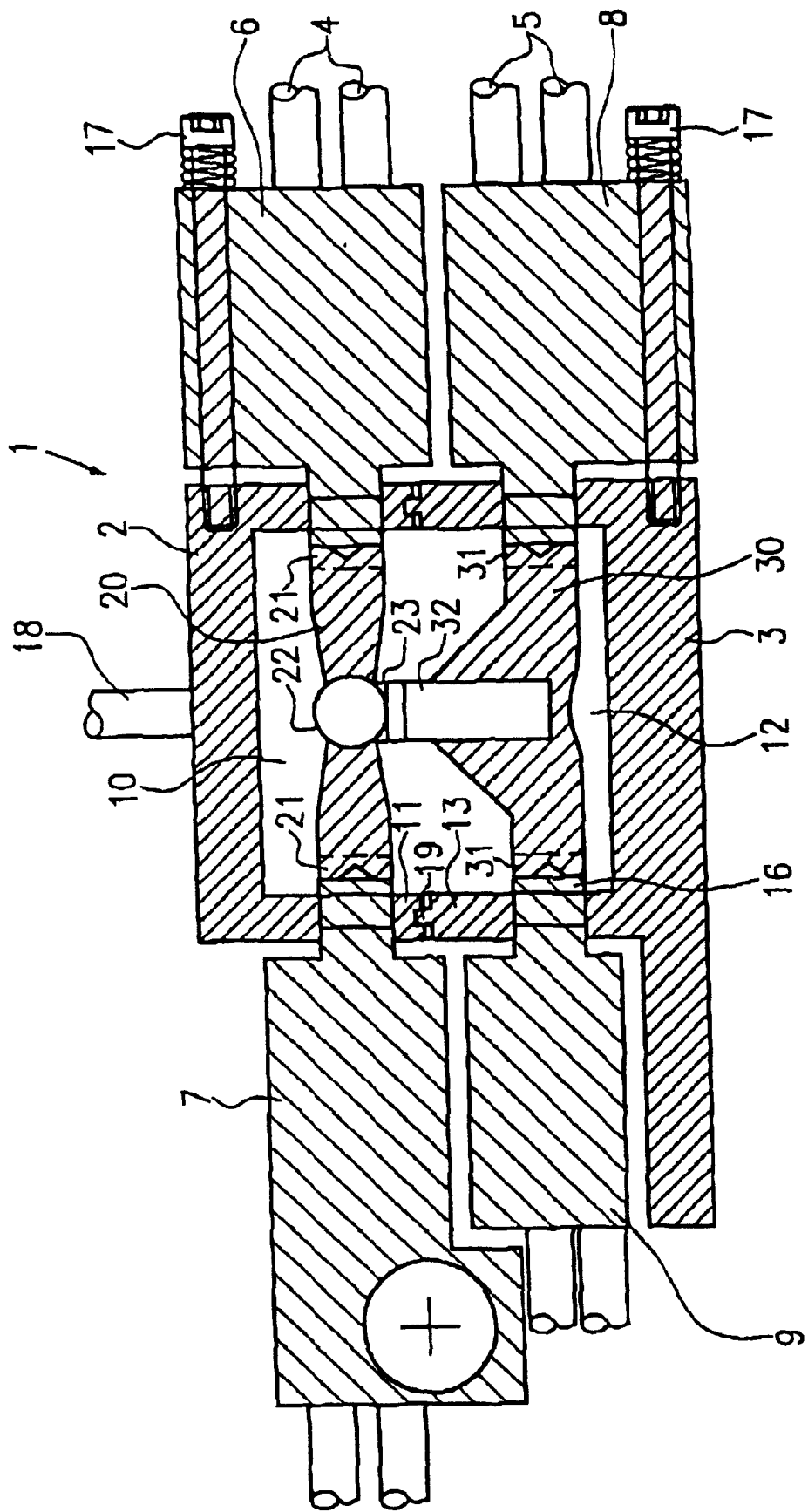
FIG. 4 is a schematic cross-section through the embodiment shown in FIG. 1 with the details shown in FIGS. 2a and 2b.

FIG. 4 is a schematic view showing the assembly described with reference to FIG. 3; here, however, the first furnace part 30 with the electrode connections 31 between the electrodes 9 and 8 is held by means of the electrode connections 16, and the second furnace part 20 on the electrode connections 21 is held by means of the electrode connections 16 between the electrodes 6 and 7. In the position of the holders 2 and 3 which is shown in FIG. 4 and corresponds to the second position, the opening of the cup 32 is in alignment with the second opening 23 of the second furnace part 20. The thermal expansion of the first and second furnace parts can be compensated by virtue of the movable electrodes 6 and 7.

During operation of furnace 1, the furnace is first rotated by a rotation of the holder 2 around the rotational axis of the drive unit 15 until the first position shown in FIG. 1 is assumed. In this position the cup 32 of the first furnace part 30 can easily be fed with a sample either automatically or manually. The sample can easily be dosed into the furnace of the invention because a large opening is provided by the cup 32. This is of particular advantage to solid samples. Subsequently, in accordance with an exemplary conventional two-step operation, the furnace 1 is rotated into the second position shown in FIGS. 3 and 4 by activation of the drive unit 15, which may be effected by either pressing a button or in a program-controlled manner. Subsequently, voltage is first advantageously applied to the electrodes 6 and 7. The sample detection tube 22 whose longitudinal axis in FIG. 4 is perpendicular to the plane of the drawing is heated to a high and constant operating temperature in a direction transverse to the longitudinal axis by the current flow produced. The first furnace part is then heated by applying a second voltage to the electrodes 8 and 9. This may take place in various steps, depending on the desired analyzing process. Since the distance between the second opening 23 and the opening of the cup 32 is set to 0.5 to 1 mm in this embodiment, the losses caused by diffusing atoms remain small. This distance remains reproducibly constant due to seal 17 during repeated feeding with various samples, so that constant conditions prevail for each analyzing operation.

Furthermore, in contrast to conventional furnaces, the invention permits the following preferred mode of operation. Directly after the cup 32 has been fed with a sample in the first position, a voltage is applied to the electrodes 8 and 9 to dry the sample in the opened state of furnace 1. Sample components exiting in this process, which are not desired during analysis, do therefore not pass into the second furnace part. After the furnace 1 has been moved into the second position, the second furnace part can be heated to the desired operating temperature and the sample is transferred accordingly by suitably heating the first furnace part.

Preferably, in accordance with the desired analytical conditions, reduced or elevated pressure can be applied through the connection piece 18 to the sample. Furthermore, it is possible to apply additional gas to the cup 32 and/or the sample detection tube 22 via the connection piece 18 or additional connection pieces, which are not shown in the figures, or by the electrodes. It is of particular advantage when a reduced pressure is applied while the furnace is cleaned, i.e. while the furnace is heated up without a sample, to support the volatilization of former sample residues. By contrast, in conventional furnaces an inadequate cleaning is often the reason for "memory" effects which considerably limit the application of the furnace technique.

Of particular advantage is that the furnace according to the invention can be used in atomic absorption spectroscopy employing continuous radiation. Since the sensitivity of the spectrometer increases in proportion with the gas pressure because of a reduced diffusion of the sample atoms out of the furnace, the dynamic range in an analysis with a continuous source can be enlarged by pressure application in the inventive furnace to a considerable extent as compared to conventional furnaces that do not allow for an operation with different gas pressures.

The present invention has been described with reference to a preferred embodiment in which the holders 2 and 3 are made of brass. However, it is possible to use any material that exhibits the required electrical and thermal characteristics, such as copper, silver, gold, etc., or corresponding compounds. Graphite has been used for the electrode connections of the electrodes 6, 7 and 8, 9 and for the electrode connections 21 of the second furnace part and for the electrode connections 31 of the first furnace part. However, it is possible to use other heat-resistant and electrically conductive materials. Furthermore, a pneumatic rotary drive which ensures a high, reproducible mechanical accuracy has been used in the above-described embodiment. However, it is also possible to use other drives with a corresponding accuracy, e.g. electric rotary motors, stepper motors, linear motors, etc. The movement which transfers the furnace 1 from the first position into the second one need not necessarily be a rotational movement. For instance, there could be provided drive means which effect a linear relative movement between the holders 2 and 3, e.g; a lift or displacement of the holders 2 and 3. Furthermore, the mechanical alignment of the second opening 23 and the cup 32 can be effected by other spacers than the ones described in this embodiment, e.g. a guide pin with an associated guide bushing, which partly consist of electrically insulating material. Furthermore, the observance of an exact distance between the first and second furnace parts and the alignment of the second opening with the cup can be ensured by the drive element alone or in combination with spacers without any guiding characteristics. The shape of the first and second furnace. parts is not limited to the shapes shown in FIGS. 2 and 4, but can expediently be modified.

What is claimed is:

1. An electrothermal furnace for an atomic absorption spectrometer for converting a sample to be analyzed into the atomized state, comprising
   a first hollow furnace part which is connected to a first pair of electrodes and includes a first opening for introducing said sample,
   a second hollow furnace part which is connected to a second pair of electrodes and includes a second opening for introducing said sample,
   a respective holder for said first and second furnace parts, and
   a drive element connected to one of said holders for automatically moving said first and second furnace parts between a first position and a second position such that in said first position said first furnace part can be fed with said sample, and that in said second position the openings of said first and second furnace parts are oriented relative to each other such that said sample can be transferred from said first furnace part into said second furnace part, a distance which is required for electrical and thermal decoupling being reproducibly defined in said second position between said first furnace part and said second furnace part.

2. The furnace according to claim 1, wherein said holders are each made movable to be rotatable or pivotable or linear relative to one another or are made movable in any desired combination thereof, said holders being only movable along a defined connection path.

3. The furnace according to claim 1, wherein said drive element comprises one of a pneumatic and an electric drive unit.

4. The furnace according to claim 1, wherein said first furnace part is arranged in a first recess in one of said holders and said second furnace part is arranged in a second recess in said other holder, said first and second recesses in said second position forming a combined cavity which is gas-tightly sealed to the environment.

5. The furnace according to claim 1, wherein said holders comprise a spacer for mechanically defining said second position.

6. The furnace according to claim 5, wherein said spacer comprises an elevated ring which defines said first recess and has a seal on one of said holders, and a recess which corresponds to said elevated ring with said seal and is provided on the other holder.

7. The furnace according to claim 5, wherein said spacer comprises a guide pin on one of said holders and a guide bushing which accurately fits said guide pin and is provided on said other holder.

8. The furnace according to claim 4, wherein one of said first and second recesses comprises at least one fluid supply opening.

9. The furnace according to claim 1, wherein said first pair of electrodes is gas-tightly connected to one of said holders and said second pair of electrodes to said other holder.

10. The furnace according to claim 1, wherein said holders comprise a cooling element.

11. A method of operating an electrothermal furnace in an atomic absorption spectrometer device, comprising the steps of:

providing an electrothermal furnace with the features according to claim 1, feeding said first furnace part in said first position with a sample, heating said first furnace part by applying a suitable voltage to said first pair of electrodes, and transferring said first and second furnace parts into said second position.

12. The method according to claim 11, wherein said first furnace part is heated in said first position to a temperature suited for drying said sample.

13. A method of operating an electrothermal furnace in an atomic absorption spectrometer, comprising the steps of:

providing an electrothermal furnace in a first position, which furnace has a first hollow furnace part that is connected to a first pair of electrodes and includes a first opening for introducing a sample, a second hollow furnace part that is connected to a second pair of electrodes and includes a second opening for introducing the sample, and a respective holder for the first and second furnace parts, feeding the first furnace part with the sample, and moving the holders from the first position to a second position in which a distance that is required for electrical and thermal decoupling is reproducibly defined between the first furnace part and the second furnace part.

14. The method according to claim 13, further comprising the step of heating the first furnace part by applying a suitable voltage to the first pair of electrodes before moving the holders from the first position to the second position.

15. The method according to claim 14, wherein the first furnace part is heated in the first position to a temperature suited for drying the sample.

* * * * *